US009347136B2

(12) United States Patent
Verrier et al.

(10) Patent No.: US 9,347,136 B2
(45) Date of Patent: May 24, 2016

(54) METHOD FOR APPLYING A COATING TO A SUBSTRATE

(71) Applicant: Pratt & Whitney Canada Corp., Longueuil (CA)

(72) Inventors: Pierre Verrier, Sainte-Julie (CA); Eric Irissou, Longueuil (CA); Frederic Belval, Sorel-Tracy (CA); Jean-Gabriel Legoux, Repentigny (CA)

(73) Assignees: PRATT & WHITNEY CANADA CORP., Longueuil (CA); NATIONAL RESEARCH COUNCIL OF CANADA, Ottawa (CA)

( * ) Notice: Subject to any disclaimer, the term of this patent is extended or adjusted under 35 U.S.C. 154(b) by 176 days.

(21) Appl. No.: 14/169,571

(22) Filed: Jan. 31, 2014

(65) Prior Publication Data

US 2015/0218704 A1   Aug. 6, 2015

(51) Int. Cl.
 *C23C 24/04*   (2006.01)
(52) U.S. Cl.
 CPC ....................................... *C23C 24/04* (2013.01)
(58) Field of Classification Search
 CPC ............................................................. C23C 24/04
 USPC ............................................................... 427/180
 See application file for complete search history.

(56) References Cited

U.S. PATENT DOCUMENTS

| 6,444,259 | B1 | 9/2002 | Subramanian et al. |
| 8,257,146 | B2 | 9/2012 | Antolotti et al. |
| 2013/0034661 | A1 | 2/2013 | Schneiderbanger et al. |
| 2013/0177705 | A1* | 7/2013 | Calla ............... C23C 24/04 427/201 |

FOREIGN PATENT DOCUMENTS

| EP | 2014415 A1 | 1/2009 |
| WO | 02/061177 | 8/2002 |
| WO | 2008/082825 | 7/2008 |
| WO | 2008/154465 | 12/2008 |

* cited by examiner

*Primary Examiner* — Xiao Zhao
(74) *Attorney, Agent, or Firm* — Norton Rose Fulbright Canada LLP

(57) ABSTRACT

A method for applying a coating to a substrate surface is provided. The method involves cold spraying a coating material against the surface of the substrate at a first velocity. The first velocity is lower in magnitude than a critical velocity. The method also involves cold spraying the coating material against the surface of the substrate at a second velocity. The second velocity is greater in magnitude than the critical velocity. The critical velocity is a threshold velocity below which the coating material is substantially deflected by the surface of the substrate and above which the coating material substantially adheres to the surface of the substrate.

20 Claims, 2 Drawing Sheets

METHOD FOR APPLYING A COATING TO A SUBSTRATE

TECHNICAL FIELD

The application relates generally to applying material, and more particularly, to a method for applying a coating to a substrate.

BACKGROUND ART

Often, a substrate such as a turbine shaft of a gas turbine engine must be prepared before it can be cold sprayed so that the material will adhere thereto. A common preparation technique is known as abrasive or grit blasting, which consists of applying an abrasive material against the substrate at a relatively high pressure so as to smooth the substrate.

One of the disadvantages of grit blasting is that the abrasive material can become embedded in the substrate, thereby contaminating the substrate, which is undesirable for substrates which require a certain material purity. Contamination of the substrate can also result because the abrasive material used is different from the coating material.

Accordingly, there exists a need for a method for applying a coating to a substrate.

SUMMARY

There is provided a method for applying a coating to a substrate surface, the method comprising: cold spraying a coating material against the substrate surface at a first velocity to modify the adhesion properties of the surface of the substrate, the first velocity being lower than a critical velocity; and cold spraying the same coating material against the substrate surface at a second velocity to adhere the coating material to the surface of the substrate to coat the substrate, the second velocity being greater than the critical velocity, wherein the critical velocity is a threshold velocity below which the coating material is substantially deflected by the surface of the substrate and above which the coating material substantially adheres to the surface of the substrate.

There is also provided a method for applying a coating to a substrate surface, the method comprising cold spraying a coating material against the substrate surface at a first velocity below a critical velocity to modify the adhesion properties of the surface, the critical velocity being a minimum velocity which results in adherence of the coating material to the surface, and then cold spraying the coating material against the surface at a second velocity above the critical velocity to coat the surface with the material.

DESCRIPTION OF THE DRAWINGS

Reference is now made to the accompanying figures in which.

DETAILED DESCRIPTION

Figure 1:
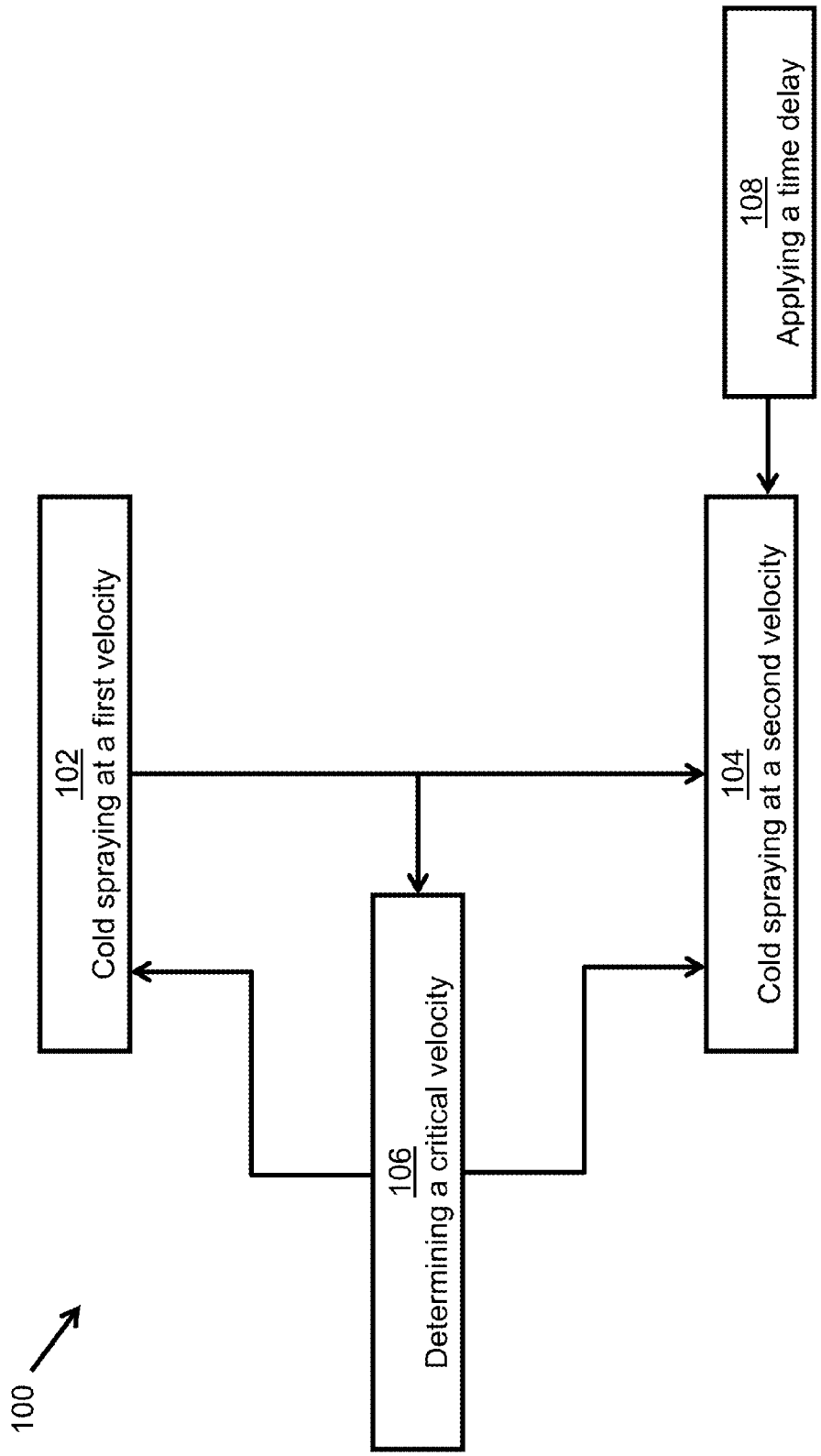
FIG. 1 is a flow diagram showing the steps of a method for applying a coating to a substrate having a surface, according to one embodiment.

There is provided a method 100 for applying a coating to a substrate having a surface, the steps of which are schematically shown in FIG. 1. Such a method 100 can be of use when it is desired to coat a substrate with a coating material. The method 100 can also be used when it is desired to prepare the substrate prior to applying the coating material. The method 100 thus allows a conditioning or "pre-treatment" of the surface of the substrate in order to enhance the deposition or coating of a cold spray of material.

The substrate can be any suitable material, and is often a metal such as hardened steel. It can be conditioned or unconditioned, such as by any suitable surface preparation technique, and can also take any form or shape which is compatible with the steps of the method 100. For example, the substrate can be the power turbine shaft or the propeller shaft of a gas turbine engine. The substrate has a surface, which can be any planar or non-planar face of the substrate that will be exposed to the coating material, and ultimately, coated.

The method includes step 102, which involves cold spraying a coating material against the surface of the substrate at a first velocity which is selected from a first range of velocities. The cold spraying of the coating material generally involves causing the coating material to impact the surface at a relatively large pressure and velocity. The magnitude and orientation of the first velocity can vary depending on numerous factors, provided that it allows the coating material to modify the adhesion properties of the surface of the substrate. Some of these factors include, but are not limited to, the coating material being used and the machine generating the cold spray. The cold spray of the coating material can optionally be applied at an angle relative to a reference plane such as the horizontal or the plane of the surface of the substrate. In most embodiments, this angle is about 90°, such that the cold spray is applied normal to the surface.

The coating material can be any suitable material which can sufficiently erode or clear the surface of the substrate when cold sprayed at the first velocity, so as to prepare the surface for receiving a coating material. This same coating material will also adhere to the substrate when cold sprayed at the second velocity discussed below. The coating material is typically in powder form, but can also be provided in another small-particle form such as pellets and grains. One possible coating material is substantially pure nickel powder.

The first velocity is selected from a first range of velocities, all of which are lower in magnitude than a critical velocity. All of the velocity values in this first range of velocities can contribute to modifying the adhesion properties of the surface of the substrate. For example, a first velocity selected from the lower end of the first range of velocities might be sufficient to erode or modify the adhesion properties of the surface, and a first velocity selected from the upper end of the first range of velocities might do so faster and more efficiently. Therefore, the selection of the first velocity value amongst this first range of velocities is highly application specific.

Determining the velocity values that comprise the first range of velocities can vary depending on numerous factors such as the coating material being used, the cold spraying apparatus, and the cold spraying environment. Generally, the first range of velocities is determined as a function of the temperature of the gas jet supplying the coating material being applied, and the pressure of the gas jet.

The critical velocity is a threshold or minimum velocity value. Below this threshold critical velocity, the cold spray of the coating material is substantially deflected by the surface of the substrate. Above this threshold critical velocity, the cold spray of the coating material substantially adheres to the surface of the substrate.

The method 100 can include the step 106 of determining the critical velocity. In most embodiments, but not necessarily all, the critical velocity is determined by cold spraying the coating material at different velocity values against multiple samples of the surface of the substrate. Each sample can then be analyzed using a suitable analytical tool, such as an electron microscope, in order to determine the effect of the impact of the particles of the coating material on the substrate. For example, if analysis of the sample at a particular velocity value reveals that a significant percentage of the particles of the coating material have bonded to the surface, then this particular velocity value is greater than the critical velocity value. Similarly, if the sample at another particular velocity value reveals that a significant percentage of the particles of the coating material have been deflected from the surface, then this particular velocity value is less than the critical velocity value. By using a sufficient number of velocity values, the critical velocity can be sufficiently approximated or determined, and used in steps 102 and 104, as shown schematically in FIG. 1. For example, a particular cold spraying application may have an average critical velocity value of about 480 m/s. Other critical velocity values are possible and within the scope of the present disclosure.

The cold spraying of the coating material at the first velocity modifies the adhesion properties of the surface of the substrate. The expression "modifies the adhesion properties" refers to the conditioning of the surface such that it can receive a coating of the coating material which better adheres thereto. This can be achieved because the impact of the coating material on the surface at a first velocity that is lower than the critical velocity can cause the material of the surface to be free of any surface scale or oxide layer. When the coating is applied to this conditioned surface at the second velocity, the coating material may have a better adhesion strength than if the surface was not so modified. The expression "modifies the adhesion properties" also refers to the effect of the impact of the coating material at the first velocity, which can partially erode or clear the surface of any contaminants that might affect the adhesion of the coating. The modification of the adhesion properties can also be achieved or enhanced by shot-peening the surface of the substrate prior to step 102. The surface of the substrate is thus prepared for the next step of the method, which involves applying the coating.

The method also includes the step 104, which involves cold spraying the same coating material against the surface of the substrate at a second velocity selected from a second range of velocities, the second velocity being greater in magnitude than the critical velocity. In so doing, the coating material will substantially adhere to the conditioned surface of the substrate.

The coating material cold sprayed in step 104 is the same as that applied in step 102. The term "same" can refer to the actual coating material used in both steps 102 and 104, such as substantially pure nickel powder. The term can also refer to the similarity in the parameters of the coating material being cold sprayed. These parameters can include, but are not limited to, coating material density, average particle size of the coating material, and average material purity. As with the cold spraying on the coating material in step 102, the coating material cold sprayed in step 104 can optionally be applied at an angle relative to the surface of the substrate, such as about 90°.

The use of the same coating material in both steps 102 and 104 advantageously reduces the likelihood of contamination which may result from the conditioning of step 102 because the coating material used for conditioning the surface is the same that is used for coating the surface. Therefore, if any particles of the coating material remain on, or are embedded in, the surface after step 102, their presence will not affect the purity or integrity of the coating formed of the same coating material. Further advantageously, the efficiency of the coating process can be improved when compared to some prior art coating techniques because the process does not need to be interrupted or delayed to change coating materials.

In the embodiment where the coating material is a powder, the powder can have an average particle size which is the same in both steps 102 and 104. This can also advantageously enhance the efficiency of the coating process because the process does not need to be interrupted or delayed in order to use powders having different average particle sizes. The importance of minimizing the delay between steps 102 and 104 is discussed below. In contrast to certain prior art devices which do not use powders having the same particle size, or which do not use the same powders in each step of their processes, the use of the same particle size and/or the same powers advantageously reduces the need to change equipment and tooling between cold spraying in steps 102 and 104, and thus minimizes the delay between these steps. An example of a non-limiting range of powder particle sizes is about 30 μm to about 80 μm.

In step 104, the coating material is cold sprayed against the surface of the substrate at a second velocity that is greater in magnitude than the critical velocity, and thus greater in magnitude than the first velocity. As with the first velocity, the second velocity is selected from the second range of velocities. Also similarly to the first velocity, all of the velocity values in this second range of velocities can contribute to adhering the coating material to the surface of the substrate. For example, a second velocity selected from the lower end of the second range of velocities might facilitate the bonding of a significant portion of the coating material to the surface and might result in a lower bond strength value. A second velocity selected from the upper end of the second range of velocities might facilitate the bonding of a greater portion of the coating material to the surface and might result in a greater bond strength value. Therefore, the selection of the second velocity value amongst this second range of velocities is also highly application specific. For example, a particular cold spraying application may have a second velocity value selected from a second range of velocities of about 560 m/s to about 770 m/s. More particularly, the second velocity value can be about 664 m/s.

The orientation of the second velocity, and the magnitude of the second range of velocities can vary depending on numerous factors, provided that it allows the coating material to adhere to the surface of the substrate, thus coating the substrate. This generally occurs when the coating material plastically deforms upon impacting the surface of the substrate. The substrate is thus coated with the coating material.

Table 1 below provides some of the possible parameters for the coating of nickel on a shot-peened substrate made of AMS6414 steel. These parameters can be used to determine the first velocity of step 102. As can be seen, the table shows possible cold sprays of a nickel coating material (designated by "CS1", "CS2", etc.). Each cold spray is associated with a pressure and a temperature of the gas jet, which allows the determination of its velocity. Alternatively, the first or second velocity can be measured directly.

TABLE 1

Cold Spray Parameters for step 102

| Sample ID | Pressure (bar) | Temperature (° C.) |
|---|---|---|
| CS1 | 20 | 130 |
| CS2 | 40 | 130 |
| CS3 | 40 | 300 |
| CS4 | 20 | 25 |
| CS5 | 20 | 25 |
| CS6 | 20 | 25 |

Figure 2:
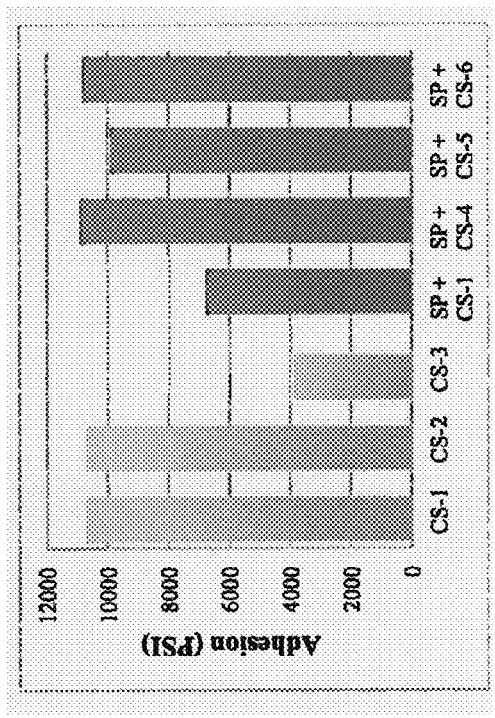
FIG. 2 is a graph showing the adhesion strength of a coating for different treatments of a surface of a substrate.

These parameters can yield the results seen in the graph of FIG. 2, which shows the adhesion strength (measured in psi) of the coating on the substrate, which was conditioned as per step 102 using some of the cold sprays of Table 1. As can be seen, it may be desirable to use cold sprays at low gas jet pressures and temperatures in order to achieve suitable adhesion strength. This trend is significant for those surfaces that had been shot-peened (designated as "SP" in FIG. 2).

Step 104 may also involve the sub step 108, which involves cold spraying the coating material at the second velocity after a time delay. The time delay can vary depending on many factors, which can include the material of the substrate, its rate of oxidation, and the environment in which the method 100 is being performed. A time delay of no more than about twenty-five minutes has been found to be acceptable for some coating materials, and it will be appreciated that the time delay can be of other durations.

The time delay is measured as of approximately the moment the cold spraying of coating material in step 102 ends. The application or observance of a time delay can be desirable, such as when it is necessary to change tooling, settings, or to inspect the substrate. However, it may not be desirable to observe too long of a time delay because that might impact process efficiency and workflows. Furthermore, waiting too long before performing step 104 may affect the adhesion strength of the coating because the surface of the substrate which was conditioned in step 102 may begin to oxidize. There is thus a need to find a suitable equilibrium between providing enough time between steps 102 and 104, and waiting too long between steps 102 and 104.

Figure 3:
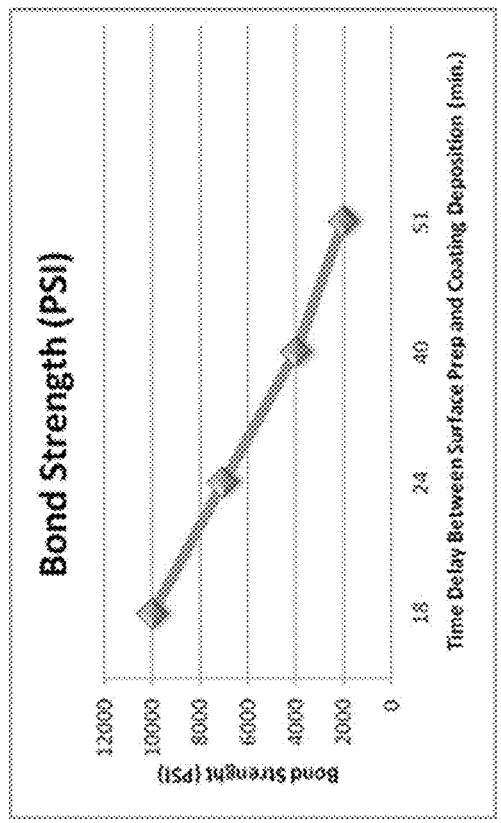
FIG. 3 is a graph showing the effect on the adhesion of a coating material when there is a delay between a first application of a cold spray and a second application of a cold spray.

FIG. 3 shows the effect that the time delay can have on the adhesion strength (shown as "Bond Strength") of the coating material to the surface of the substrate, for some applications of the method 100. As can be seen, the adhesion strength of the coating material to the surface of the substrate generally deteriorates if too long of a delay is observed between steps 102 and 104. It was observed that too long of a time delay may lead to a coating having insufficient adhesion strength. Indeed, in some instances, the adhesion strength can decrease by a factor of five if the delay is increased from about ten minutes to about fifty minutes.

It will be appreciated that the steps of the above-described method can be varied or interchanged without departing from the scope of the present disclosure.

The above description is meant to be exemplary only, and one skilled in the art will recognize that changes may be made to the embodiments described without departing from the scope of the invention disclosed. Modifications which fall within the scope of the present invention will be apparent to those skilled in the art, in light of a review of this disclosure, and such modifications are intended to fall within the appended claims.

The invention claimed is:

1. A method for applying a coating to a substrate surface, the method comprising:
   cold spraying a coating material against the substrate surface at a first velocity to modify the adhesion properties of the surface of the substrate, the first velocity being lower than a critical velocity; and
   cold spraying the same coating material against the substrate surface at a second velocity to adhere the coating material to the surface of the substrate to coat the substrate, the second velocity being greater than the critical velocity, wherein the critical velocity is a threshold velocity below which the coating material is substantially deflected by the surface of the substrate and above which the coating material substantially adheres to the surface of the substrate.

2. A method as defined in claim 1, wherein cold spraying the same coating material comprises cold spraying the coating material after a time delay.

3. A method as defined in claim 2, wherein cold spraying the coating material after a time delay comprises cold spraying the coating material with the time delay being a maximum of about twenty-five minutes.

4. A method as defined in claim 1, wherein cold spraying the coating material comprises cold spraying the coating material at an angle of about 90° to the surface of the substrate.

5. A method as defined in claim 1, wherein cold spraying the coating material comprises cold spraying a powder having an average particle size, the average particle size of the powder being substantially the same at the first and second velocity.

6. A method as defined in claim 1, wherein cold spraying the coating material comprises cold spraying substantially pure nickel powder.

7. A method as defined in claim 1, further comprising determining the critical velocity.

8. A method as defined in claim 7, wherein determining the critical velocity comprises cold spraying the coating material against multiple samples of the surface, each sample being cold sprayed at a different velocity.

9. A method as defined in claim 8, wherein determining the critical velocity further comprises analyzing each sample of the surface to determine a percentage of particles of the coating material having adhered to said sample.

10. A method as defined in claim 9, wherein determining the critical velocity further comprises comparing the percentage of particles of the coating material having adhered to said sample to a threshold percentage value.

11. A method as defined in claim 1, wherein cold spraying the coating material comprises using a critical velocity of about 480 m/s.

12. A method as defined in claim 1, further comprising shot-peening the surface of the substrate prior to cold spraying the coating material at the first velocity.

13. A method for applying a coating to a substrate surface, the method comprising cold spraying a coating material against the substrate surface at a first velocity below a critical velocity to modify the adhesion properties of the surface, the critical velocity being a minimum velocity which results in adherence of the coating material to the surface, and then cold spraying the coating material against the surface at a second velocity above the critical velocity to coat the surface with the material.

14. A method as defined in claim 13, wherein cold spraying the coating material at the second velocity comprises cold spraying the coating material after a time delay, the time delay being a maximum of about twenty-five minutes.

15. A method as defined in claim 13, wherein cold spraying the coating material comprises cold spraying the coating material at an angle of about 90° to the substrate surface.

16. A method as defined in claim 13, wherein cold spraying the coating material comprises cold spraying a powder coating material, the powder coating material having an average particle size, the average particle size of the powder coating material being substantially the same at the first and second velocity.

17. A method as defined in claim 13, wherein cold spraying the coating material comprises cold spraying substantially pure nickel powder at the first and second velocity.

18. A method as defined in claim 13, further comprising determining the critical velocity, wherein determining the critical velocity comprises cold spraying the coating material against multiple samples of the surface, each sample being cold sprayed at a different velocity.

19. A method as defined in claim 18, wherein determining the critical velocity further comprises analyzing each sample of the surface to determine a percentage of particles of the coating material having adhered to said sample, and comparing the percentage of particles to a threshold percentage value.

20. A method as defined in claim 13, further comprising shot-peening the substrate surface prior to cold spraying the coating material at the first velocity.

* * * * *